United States Patent [19]
Wagner et al.

[11] 4,207,330
[45] * Jun. 10, 1980

[54] METHOD FOR TREATING HYPERGLYCEMIA IN MAMMALS USING ARYLAMINO BENZOIC ACIDS

[75] Inventors: Eugene R. Wagner, Carmel; Roger D. McDermott, Noblesville, both of Ind.

[73] Assignee: The Dow Chemical Company, Midland, Mich.

[*] Notice: The portion of the term of this patent subsequent to Mar. 6, 1996, has been disclaimed.

[21] Appl. No.: 13,845

[22] Filed: Feb. 22, 1979

Related U.S. Application Data

[63] Continuation-in-part of Ser. No. 922,002, Jul. 3, 1978, Pat. No. 4,143,151.

[51] Int. Cl.$^2$ .............................................. A61K 31/38
[52] U.S. Cl. .................................................... 424/275
[58] Field of Search .......................................... 424/275

[56] References Cited

U.S. PATENT DOCUMENTS

| | | | |
|---|---|---|---|
| 3,674,843 | 7/1972 | Shen et al. | 424/310 X |
| 3,983,164 | 9/1976 | Thorne et al. | 424/324 X |

FOREIGN PATENT DOCUMENTS 7602332   9/1976   Netherlands ............................ 424/310

OTHER PUBLICATIONS

Chemical Abstracts, vol. 86, 1977, 294994.

*Primary Examiner*—Frederick E. Waddell

[57] ABSTRACT

A method for treating hyperglycemia in a mammal which comprises administering internally to said mammal a hypoglycemic amount of an arylamino benzoic acid or pharmaceutically-acceptable salt thereof, wherein aryl represents phenyl, substituted phenyl, thienyl or substituted thienyl.

1 Claim, No Drawings

METHOD FOR TREATING HYPERGLYCEMIA IN MAMMALS USING ARYLAMINO BENZOIC ACIDS

CROSS-REFERENCE TO RELATED APPLICATIONS

This application is a continuation-in-part of copending U.S. Patent Application Ser. No. 922,002, filed July 3, 1978, now U.S. Pat. No. 4,143,151.

BACKGROUND OF THE INVENTION

Diabetes mellitus is a disease of mammals which is characterized by an intolerance to carbohydrates and an inadequate production and secretion of insulin by the β-cells in the islets of Langerhans. The disease is often associated with vascular degeneration, especially atherosclerosis. Hypoglycemic agents which are effective in lowering blood sugars may be used in the treatment of certain types of diabetes. U.S. Pat. No. 3,983,164 describes a group of benzoic acid derivatives which have demonstrated hypoglycemic activity.

Dutch publication No. 7,602,332 describes various related derivatives of benzoic acid which are useful as hypolipidemic agents.

SUMMARY OF THE INVENTION

The present invention relates to a method for lowering blood sugar in a mammal which comprises administering internally to the mammal an effective hypoglycemic amount of a compound having the general formula

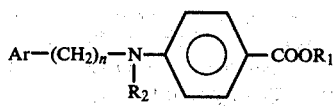

wherein $R_1$ represents hydrogen or a lower alkyl; $R_2$ represents hydrogen or methyl; n represents an integer of from 0 to 3; and Ar represents phenyl, thienyl, halo substituted thienyl, or substituted phenyl wherein the substituted moieties are selected from the group consisting essentially of halo, lower alkyl, and trihalomethyl.

As used herein the term lower alkyl refers to an alkyl containing from 1 to about 3 carbon atoms, either branched or unbranched. The term lower alkyl thus includes, for example, methyl, ethyl, propyl, and isopropyl. The term halo refers to a halogen substitution selected from the group consisting essentially of fluoro, chloro, bromo, and iodo with fluoro and chloro substitutions being particularly preferred.

Pharmaceutically-acceptable salts of the arylaminobenzoic acid compounds described herein are considered as being within the scope of the invention. Pharmaceutically-acceptable salts refer to the acid addition salts of those bases which will form a salt with the carboxylic acid and which will not cause an adverse physiological effect when administered to an animal at dosages consistent with good pharmacological activity. Suitable bases thus include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary, and tertiary amines and the like. Also aluminum salts of the instant compounds may be obtained by treating the corresponding sodium salt with an appropriate aluminum complex such as, for example, aluminum chloride hexahydrate, and the like.

The arylaminobenzoic acids described above, their esters and pharmaceutically-acceptable salts when used according to the method of the present invention show hypoglycemic activity in mammals, i.e. lower the level of sugar in the blood. The compounds used in the practice of the present invention are therefore particularly suitable for use in the treatment of diabetes in mammals characterized by abnormally high levels of sugar in the blood. The compounds can be administered internally to the mammal either orally or parenterally by subcutaneous, intravenous, or intraperitoneal injection or by implantation or the like. Oral administration is generally preferred.

The effective hypoglycemic amount of the active compounds to be internally administered to a mammal, that is the amount which is effective to significantly lower the amount of sugar in the blood, can vary depending upon such factors as the particular arylaminobenzoic acid, ester, or pharmaceutically-acceptable salt employed, the desired level of blood sugar to be obtained, the severity of the disease, the period of administration, and the method of administration. In general, an effective daily dosage range is from about 7 to about 180 milligrams per kilogram of body weight, with a daily dosage range of from about 7 to about 60 milligrams per kilograms of body weight being preferred.

DETAILED DESCRIPTION OF THE INVENTION

The compounds used in the practice of the present invention are prepared by condensing a pre-selected aryl aldehyde with p-aminobenzoic acid or an ester thereof. The resulting Schiff base is reduced to prepare the corresponding free acid. A convenient method of carrying out the latter procedure involves mixing about 0.1 mol. of the Schiff base with an excess of ethanol and water. Dilute aqueous sodium hydroxide in an amount of about 0.1 molar equivalent of the Schiff base optionally can be added to the mixture. Sodium borohydride or other suitable reducing agent (0.1 ml) is added at about room temperature and stirred until it dissolves. The mixture is heated at reflux for about 1 or 2 hours. The product may be separated from the mixture by known procedures and further purified if desired.

Pharmaceutically-acceptable salts of the acid may be prepared by treating the free acid with an appropriate base, that is a base which will form a pharmaceutically-acceptable salt with the carboxylic acid and the anions of which are relatively innocuous at dosages consistent with good pharmacological activity so that the desired hypoglycemic properties of the salt are not vitiated by side effects ascribable to the anions.

Examples of compounds prepared using the above method of preparation and having hypoglycemic properties are given in the Table below.

In carrying out the method of the present invention, the active compound can be administered directly or as an active ingredient of a pharmaceutical preparation or composition. To illustrate, for oral administration, pharmaceutical preparations of the arylaminobenzoic acids may be made by following the conventional techniques of the pharmaceutical chemist. These techniques involve granulating and compressing the active compound alone or in admixture with other materials or variously mixing and dissolving or suspending the active compound with other ingredients as appropriate to prepare a predetermined end product. Numerous pharmaceutical forms to carry the compound can be used. For example, the pure compound can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linquets, powders, capsules, troches or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate, disintegrating agents such as maize starch or alginic acid, and lubricating agents such as magnesium stearate may be used.

If a liquid carrier is used, the preparation may be in the form of a soft gelatin capsule, a syrup, a liquid solution or a suspension.

The hydrocarbon solubility of the compounds of this invention generally is sufficiently high to allow the use of pharmaceutically-acceptable oils either as a solvent or as a carrier. For example vegetable or animal oils such as sunflower oil, safflower oil, maize oil or cod liver oil can be used. Glycerine can also be used. With this latter solvent, for 2 to 30 percent water may be added. When water alone is the carrier, or when the solubility of the compound in the oil is low, the preparations can be administered in the form of a slurry.

Emulsion compositions may be formulated using emulsifying agents such as sorbitan trioleate, polyoxyethylene sorbitan monooleate, lecithin, gum acacia or gum tragacanth. Aqueous based suspensions may be prepared with the aid of wetting agents such as polyethylene oxide condensation products of alkylphenols, fatty alcohols or fatty acids with the suspending agents, for example a hydrophilic colloid such as polyvinylpyrrolidone. The emulsions and suspensions may contain conventional excipients such as sweetening agents, flowing agents, coloring materials and preservatives.

The arylamino benzoic acids, ester or salt used in the method of the present invention also can be incorporated in a nutritive foodstuff such as, for example, margarine, edible oils, casein, carbohydrates and the like. Such nutritive compositions are adapted to be administered as a partial or total diet or as a supplement to the diet. Such compositions preferably contain from about 0.02 or less to about 2.0 or more percent of the active ingredient when administered as the total diet. The compositions can contain higher concentrations of the active ingredient when administered as a supplement.

For parenteral use, the compounds of this invention can be formulated with sterile ingredients, compounded and packaged asceptically. They may be administered intravenously or intramuscularly. Useful solvents for formulation in such use are the polyhydric aliphatic alcohols and mixtures thereof. Especially satisfactory are the pharmaceutically-acceptable glycols, such as propylene glycol, and mixtures thereof. Glycerine is another example of a polyol which is particularly useful. Up to 25–30 percent by volume of water may be incorporated in the vehicle if desired. An 80 percent aqueous propylene glycol solution is a particularly convenient solvent system. A pH range, about 7.4, and isotonicity compatible with body isotonicity, is desirable. Basicity may be controlled by addition of a base as required, and a particularly convenient base is monoethanolamine. It may often be desirable to incorporate a local anesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g. at least 1 percent and preferably at least 5 percent, are preferred as they allow for the easier administration of the compound.

The hypoglycemic activity of the subject compounds was demonstrated in alanine-induced hypoglycemic mice. Alanine is the most glucogenic of the amino acids and also stimulates gluconeogensis in normal animals. Animals suffering from diabetes show an exaggerated hyperglycemic response to a protein or amino acid meal, therefore the hyperglycemic state induced by alanine closely parallels the response of a diabetic mammal.

Studies demonstrating the hypoglycemic activity of the subject compounds were carried out by interpertioneally injecting fasted male Swiss-Webster mice with 60 mg/kg of body weight of the active compound. Fifteen minutes later the same mice were injected intrapertioneally with 10 m moles/kg body weight of L-alanine. Sixty minutes after injection of the active compound, the animals were sacrificed and their sera were analyzed for glucose. The control consisted of both fasted mice and mice injected with alanine. The results are expressed as percent lowering of serum glucose from the alanine induced hyperglycemic level to the fasted control glucose level, i.e. lowering to the fasting glucose level is 100% lowering.

The results obtained using the method described above is given in the following Table.

TABLE

| Example No. | Compound Name | % Lowering Blood Sugar* |
|---|---|---|
| 1 | p-anilinobenzoic acid | 88 |
| 2 | 4-(((4-(1-methylethyl)phenyl)methyl)amino)benzoic acid | 78 |
| 3 | 4-(((4-chlorophenyl)methyl)amino)benzoic acid | 111 |
| 4 | 4-(((4-methylphenyl)methyl)amino)benzoic acid | 144 |
| 5 | 4-(((4-ethylphenyl)methyl)amino)benzoic acid | 96 |
| 6 | 4-(((4-fluorophenyl)methyl)amino)benzoic acid | 110 |
| 7 | 4-((2-thienylmethyl)amino)benzoic acid ethyl ester | 78 |
| 8 | 4-((2-thienylmethyl)amino)benzoic acid | 51 |
| 9 | 4-(((3-chlorophenyl)methyl)amino)benzoic acid | 64 |
| 10 | 4-((3-phenylpropyl)amino)benzoic acid | 99 |
| 11 | 4-(((4-(trifluoromethyl)phenyl)methyl)amino)benzoic acid | 106 |

TABLE-continued

| Example No. | Compound Name | % Lowering Blood Sugar* |
|---|---|---|
| 12 | 4-(((4-chlorophenyl)methyl)amino)benzoic acid sodium salt | 129 |
| 13 | 4-(((3-fluorophenyl)methyl)amino)benzoic acid | 52 |
| 14 | 4-(((4,5-dichloro-2-thienyl)methyl)amino)benzoic acid | 83 |
| 15 | 4-(((5-bromo-2-thienyl)methyl)amino)benzoic acid | 210 |

*as compared to control group.

The results demonstrate the hypoglycemic activity of representative compounds falling within the scope of the present invention. Those compounds wherein the substitution is halo or lower alkyl are preferred as are those compounds wherein Ar represents substituted phenyl.

The effective dose ($ED_{50}$) of several of the subject compounds were determined. The following compounds showed the lowest $ED_{50}$'s of the compounds actually tested and therefore represent preferred embodiments of the invention.

| Compound Example No. | $ED_{50}$* in mg/kg body weight |
|---|---|
| 3 | 11 |
| 4 | 15 |
| 5 | 15 |
| 12 | 6 |
| 15 | 4.6 |

*effective dose represents the amount of the active ingredient required to obtain a 50% reduction in serum glucose as compared to the control animals.

The compound 4-(((5-bromo-2-thienyl)methylamino)benzoic acid (Example 15) showed the highest activity as a hypoglycemic agent of the compounds tested, and represents the preferred embodiment of the present invention. This compound continued to show significant hypoglycemic activity in mice at dosages as low as 7.5 mg per kg of body weight.

What is claimed is:

1. A method for treating hyperglycemia in a mammal which comprises administering internally to said mammal an effective hypoglycemic amount of the compound 4-(((5-bromo-2-thienyl)methyl)amino)benzoic acid or pharmaceutically-acceptable salt thereof.

* * * * *